US006780155B2

(12) United States Patent
Li

(10) Patent No.: US 6,780,155 B2
(45) Date of Patent: Aug. 24, 2004

(54) METHOD AND SYSTEM FOR ULTRASOUND BLOOD FLOW IMAGING AND VOLUME FLOW CALCULATIONS

(75) Inventor: Xiang-Ning Li, Mill Creek, WA (US)

(73) Assignee: Koninklijke Philips Electronics (NL)

( * ) Notice: Subject to any disclaimer, the term of this patent is extended or adjusted under 35 U.S.C. 154(b) by 0 days.

(21) Appl. No.: 10/025,398

(22) Filed: Dec. 18, 2001

(65) Prior Publication Data

US 2003/0114756 A1 Jun. 19, 2003

(51) Int. Cl.[7] ................................................ A61B 8/06
(52) U.S. Cl. ....................................................... 600/454
(58) Field of Search ................................ 600/437, 438, 600/439, 440, 441, 442, 443, 444–458; 128/916; 367/7, 11, 130, 138; 73/625, 626

(56) References Cited

U.S. PATENT DOCUMENTS

| | | | | |
|---|---|---|---|---|
| 5,105,817 A | * | 4/1992 | Uchibori et al. | 600/454 |
| 5,285,788 A | * | 2/1994 | Arenson et al. | 600/441 |
| 5,623,930 A | | 4/1997 | Wright et al. | 128/661.1 |
| 5,701,898 A | * | 12/1997 | Adam et al. | 600/454 |
| 5,720,291 A | | 2/1998 | Schwartz | 128/661.1 |
| 5,769,079 A | * | 6/1998 | Hossack | 600/454 |
| 5,967,987 A | * | 10/1999 | Sumanaweera et al. | 600/454 |
| 5,997,480 A | * | 12/1999 | Sumanaweera et al. | 600/454 |
| 6,071,242 A | * | 6/2000 | Lin | 600/456 |
| 6,117,080 A | | 9/2000 | Schwartz | 600/443 |
| 6,190,321 B1 | * | 2/2001 | Pang et al. | 600/441 |
| 6,241,675 B1 | | 6/2001 | Smith et al. | 600/443 |
| 6,258,029 B1 | | 7/2001 | Guracar et al. | 600/443 |

OTHER PUBLICATIONS

Brandberg et al., Joakim, "Increased Accuracy of Echocardiographic Measurement of Flow Using Automated Spherical Integration of Multiple Plane Velocity Vectors," Ultrasound In Med. & Biol., vol. 25, No. 2, pp. 249–257, 1999.

Kim et al., Won Yong, "A New Doppler Method for Quantification of Volumetric Flow: In Vivo Validation Using Color Doppler," Journal of the American College of Cardiology, vol. 27, No. 1, pp. 182–192, Jan. 1996.

Sun et al., Ying, "Estimation of Volume Flow Rate by Surface Integration of Velocity Vectors for Color Doppler Images," Journal of the American Society of Echocardiography, vol. 8, No. 6, pp. 904–914, Nov.–Dec. 1995.

* cited by examiner

Primary Examiner—Ali Imam
(74) Attorney, Agent, or Firm—Dorsey & Whitney LLP

(57) ABSTRACT

An ultrasound imaging method and system includes a two-dimensional array transducer scanhead coupled to a beamformer. The beamformer and scanhead obtain signals corresponding to ultrasound echoes reflected from a measurement volume extending across a blood vessel. The signals are processed by a Doppler processor to generate data corresponding to a three-dimensional Doppler image of blood flow velocity in the sample volume. The signals are also processed by a B-mode processor to generate data corresponding to a cross section through the vessel. An image processor transforms the data corresponding to the three-dimensional Doppler image to data corresponding to a projection of the three-dimensional Doppler image onto a plane. The image processor also combines the transformed Doppler data with the B-mode data to create a composite image. Volume flow rate can also be determined by integrating the flow velocity in the projection of the three-dimensional Doppler image.

33 Claims, 4 Drawing Sheets

METHOD AND SYSTEM FOR ULTRASOUND BLOOD FLOW IMAGING AND VOLUME FLOW CALCULATIONS

TECHNICAL FIELD

This invention relates to the field of diagnostic ultrasound, and, more particularly, to a method and system that can accurately estimate the flow volume of a vessel without requiring knowledge of the vessel shape or angular orientation.

BACKGROUND OF THE INVENTION

Ultrasound can be used to image tissues and vessels using a variety of imaging modalities. For example, B-mode scanning can be used to image tissues by portraying the tissues in a gray scale in which the brightness of each region in the image is a function of the intensity of ultrasound returns from corresponding regions of the tissues. B-mode scanning can be used to visualize the shapes of organs and vessels, and to detect the presence of masses, such as tumors, in tissues.

Doppler scanning can be used to provide images showing the velocity of moving sound scatterers, such as blood flowing through an artery or vein. Using Doppler scanning to image the flow pattern of blood through a vessel allows the blood flow velocities and the internal shape of the vessel to be imaged and quantified. As a result, stenoses due to partial obstructions in blood vessels can be detected.

Attempts have also been made to measure volume flow rate, i.e., the volume of fluid flow, using Doppler scanning. Volume flow measurements can be important to determine, for example, cardiac output. In one prior art approach, a phased array scanhead is used to obtain a plurality of spaced-apart Doppler scan lines in a cross-section of the vessel. The scanlines are then combined to create a two-dimensional image depicting the velocity of blood flow through the vessel. The velocity of blood flowing through the vessel can then be integrated across the area of the vessel to determine the volume flow rate. To operate from multiple positions in an acceptable timeframe, the number of scan planes must be limited to a value that results in the scan planes being significantly spaced apart from each other. As a result, much of the flow information depicted in the image area is obtained by interpolating between adjacent planes. Since blood flow through a vessel can be highly irregular, there can be no assurance that the mean velocity values accurately depict the actual blood flow in the regions between the scan planes. Furthermore, measured flow velocity differs from the actual flow velocity by the cosine of the angle between the ultrasound beam and the flow direction. Yet is often difficult to accurately determine the direction of blood flow. Thus, conventional Doppler imaging using a two dimensional approach often does not provide an accurate depiction of blood flow.

As previously mentioned, volume flow rate of blood in a vessel is the blood flow velocity integrated across the area of the blood vessel. Thus, inaccuracies in measuring blood velocity using conventional, two dimensional Doppler imaging correspondingly affect the accuracy of blood volume flow rate determinations.

The above-described limitations in measuring blood volume flow using conventional, multiple scanline Doppler imaging techniques has resulted in the development of improved techniques for measuring and depicting blood flow rate. According to one technique described in U.S. Pat. No. 5,623,930 to Wright et al., blood flow velocity through a vessel is measured in several planes intersecting the vessel at different angles. By processing this blood flow velocity data, blood volume flow can be determined without knowing the angle between the ultrasound beam and the direction of blood flow. However, the needed geometric assumption and the need to obtain blood velocity measurements in several planes would appear to limit the usefulness of this technique.

Another approach described in publications by Kim et al., entitled "*A New Doppler Method for Quantification of Volumetric Flow: In Vivo Validation Using Color Doppler,*" Journal of the American College of Cardiology, 1996, and by Brandberg et al., entitled "*Increased Accuracy of Echocardiographic Measurement of Flow Using Automated Spherical Integration of Multiple Plane Velocity Vectors,*" Ultrasound In Med. & Biol., 1999, is able to directly measure and image blood volume flow rate without the need to know the angle between the ultrasound beam and the blood flow direction. With reference to FIG. 1, the volume flow rate of blood through a blood vessel 10 can be measured by measuring the volume flow rate through any arbitrary sample surface 14 passing through the vessel. The volume flow rate through the sample surface 14 can be measured by first determining the velocity of blood flowing through the sample surface 14 by performing a three-dimensional Doppler scan. The velocity is then integrated throughout the area of the sample surface 14.

The reason the surface 14 need not be particularly oriented is that whatever volume of blood flows through any surface or plane extending through the vessel 10 also flows through the sample surface 14. Thus, the sample surface 14 can be any arbitrary shape having any arbitrary orientation to the flow of blood through the vessel 10. In practice, as shown in FIG. 2, a spherical sample surface 20 is obtained by obtaining a three-dimensional Doppler image in a narrow sample volume 22 equidistant from a two-dimensional array scanhead 24. A Doppler scan of this type is in this context referred to as Flow-mode, or F-mode, scanning. A 3-D flow image 26 obtained by an F-mode scan is shown in FIG. 3. As shown therein, the 3-D flow image 26 is rendered as a spherical cross section 28 through the blood vessel 10 corresponding to the spherical sample surface 20. Although the flow rate of blood can be determined using F-mode scanning, it is difficult to portray the flow velocity in the spherical cross-section 28. Among other factors, it is difficult to render a three-dimensional surface in the two-dimensions available in a conventional display. The need to render an image in three dimensions also requires a relatively large amount of processing time, thus making it difficult to provide real time volume flow images. Furthermore, it is more complicated to compute the data on the spherical surface along with the desired user interactions indicating the flow region of interest.

Another difficulty with the flow imaging technique exemplified by FIG. 2 is delineating the boundary between the blood flow and the wall of the vessel 10. This process, known as segmentation, is important for defining the area over which the flow velocity will be integrated. If segmentation does not include all of the blood flow, the volume flow measurements will be inaccurate. If the segmentation includes surrounding flow events, integration will occur over areas that need not be integrated, thereby increasing the acquisition and processing time needed to determine blood volume flow rate. Also, if the segmentation encompasses an area occupied by other blood vessels, volume flow calculations may be inaccurate. Segmentation is currently accomplished in most cases by identifying control points on the boundary between the blood flow and the vessel 10. The ultrasound monitor then connects the control points to complete the segmentation process. Accurate segmentation requires a large number of control points, thus making this segmentation technique very time consuming. Also, it can be difficult to accurately identify the boundary between the blood flow and the vessel wall.

There is therefore a need for a method and apparatus that can accurately portray blood flow in two dimensions so that volume flow rate can be easily and quickly calculated, and which can quickly and easily segment the image to delineate the boundary between blood flow and vessel walls.

SUMMARY OF THE INVENTION

A method and system for generating an ultrasound image shows the velocity of blood flowing through a blood vessel and calculates the volume flow of the blood. A two-dimensional ultrasound transducer array or a moving one-dimensional array is used to obtain a three-dimensional Doppler image of blood flow velocity in a relatively narrow measurement volume. The measurement volume intersects the blood vessel a fixed distance from the transducer. The Doppler data of the measurement volume is then electronically projected onto a planar surface to create a two-dimensional blood flow velocity image that can be viewed on a display. The volume flow rate of the blood flowing through the vessel can be determined by integrating the blood flow velocity within the two-dimensional blood flow velocity image. A cross section of the blood vessel obtained by B-mode scanning can be superimposed on the two-dimensional blood flow velocity image.

DETAILED DESCRIPTION OF THE INVENTION

Figure 1:
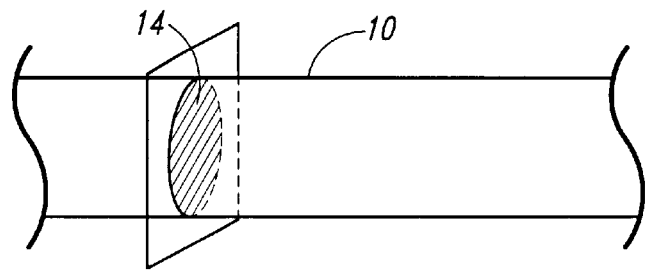
FIG. 1 is a schematic view illustration of the manner in which volume flow through an arbitrary sample surface can be determined.
Figure 2:
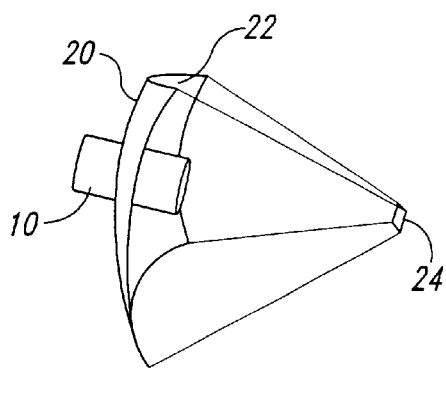
FIG. 2 is a schematic view illustration the manner in which volume flow through a spherical sample surface is determined using three-dimensional Doppler imaging.
Figure 3:
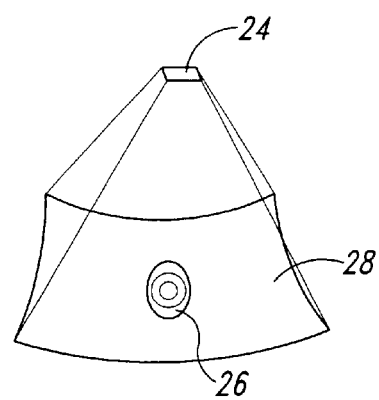
FIG. 3 is a schematic view illustration an F-mode image that can be obtained from an F-mode scan as illustrated in FIG. 2.
Figure 4:
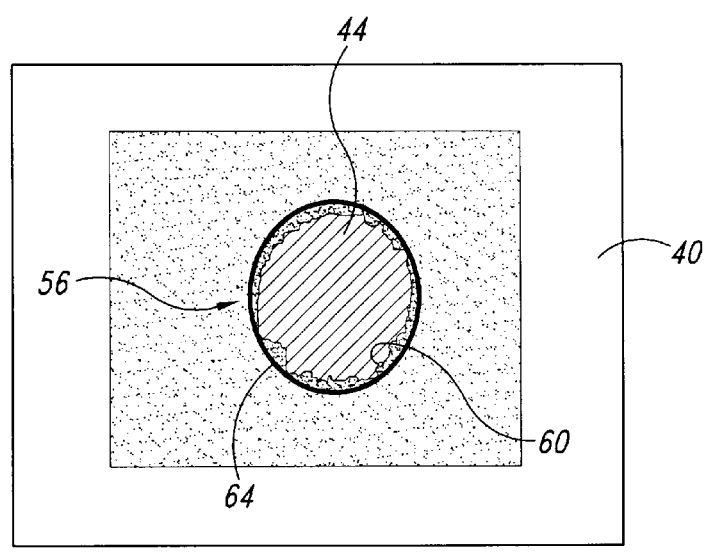
FIG. 4 is a schematic view of a 2-D volume flow image obtained by an ultrasound imaging system according to one embodiment of the invention.

One embodiment of the invention uses the technique of Doppler scanning in a narrow measurement volume 22 equidistant from the transducer 24, as shown in FIGS. 2 and 3. The transducer 24 is preferably a two-dimensional array transducer that is capable of performing a three-dimensional F-mode Doppler scan. Like the technique shown in FIGS. 2 and 3, the 3-D volume flow image 26 resulting from the F-mode scan is a set of velocity vectors in a spherical cross section 28 for a range at which the size of the transducer approximates a point source. Optimally, the velocity is estimated at every point on the nonplanar surface 28 by beams which are normal to the surface at the points where the velocity estimations are made. However, unlike the technique shown in FIGS. 2 and 3, one embodiment of the invention electronically projects the nonplanar 3-D flow image 26 onto a two-dimensional image plane 40 to form a 2-D flow image 44, as shown in FIG. 4. By creating a 2-D flow image 44, the flow image 44 can be rendered with significantly less processing power than is required to render the original 3-D flow image 26. As a result, user interaction can be easily rendered with real time processing.

With further reference to FIG. 4, an embodiment of the invention that will be explained with reference to FIG. 6 also obtains a B-mode image 56 of the vessel 10 and surrounding tissue in the vicinity of the spherical sample surface 20, and superimposes the B-mode image 56 onto the 2-D flow image 44 obtained by projecting the 3-D flow image 26 onto a plane. As a result, a boundary 60 between the blood flow shown in the 2-D flow image 44 and the walls of the vessel 10 shown in the B-mode image 56 is readily apparent. It is therefore relatively easy to conventionally segment the image to delineate the area of blood flow.

Figure 5A:
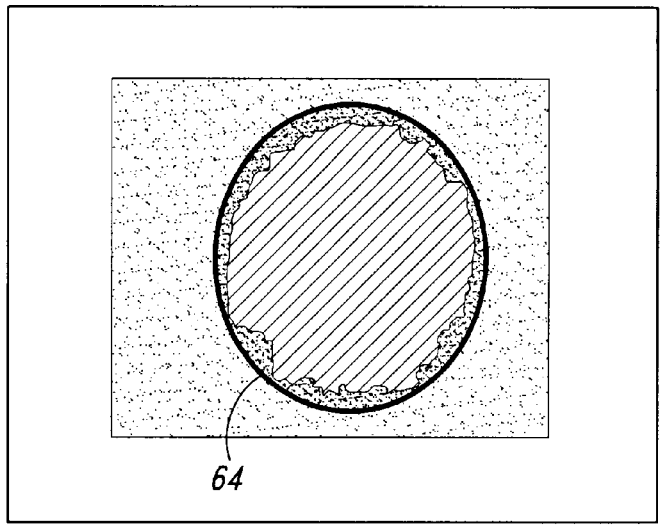
FIGS. 5A–D are schematic view illustrating a segmenting template created by an ultrasound imaging system according to one embodiment of the invention, and illustrating various ways in which the template can be manipulated.
Figure 5B:
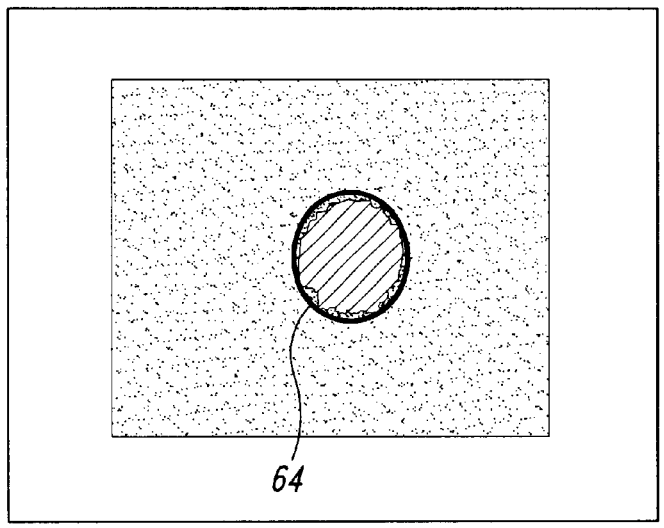
Figure 5C:
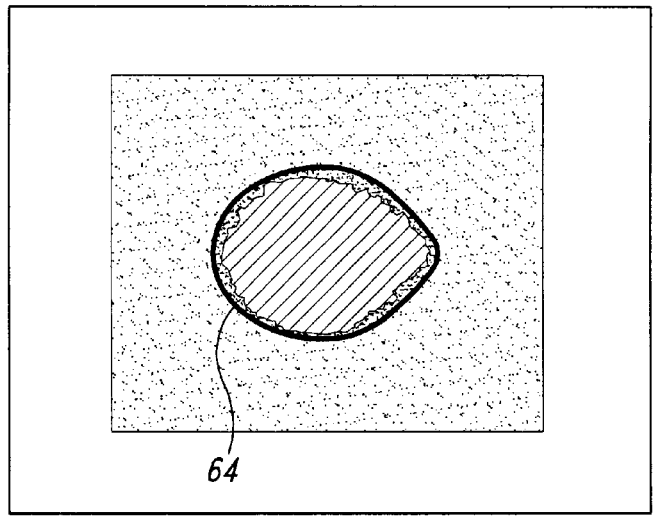
Figure 5D:
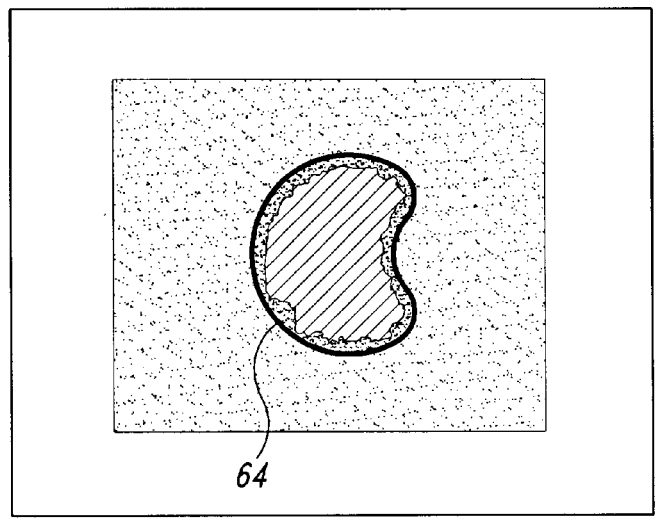

To make it even easier to segment the boundary between the blood flow and the vessel wall, the embodiment of the invention that will be explained with reference to FIG. 6 automatically creates a template 64 delineating the boundary, as shown in FIG. 4. The template 64 can then be manipulated by either scaling it to a larger or smaller size, as shown in FIGS. 5A and 5B, or by expanding it or contracting it in specific areas, as shown in FIGS. 5C and 5D. The template 64 can be expanded or contracted in specific areas by various means, such as by selecting a specific point on the template 64 with a pointing device (not shown) and then moving the point in the desired direction. The template 64 will then be automatically adjusted to encompass the moved point. This technique for adjusting an electronically drawn boundary outline is more fully described in U.S. Pat. No. 6,491,636.

Figure 6:
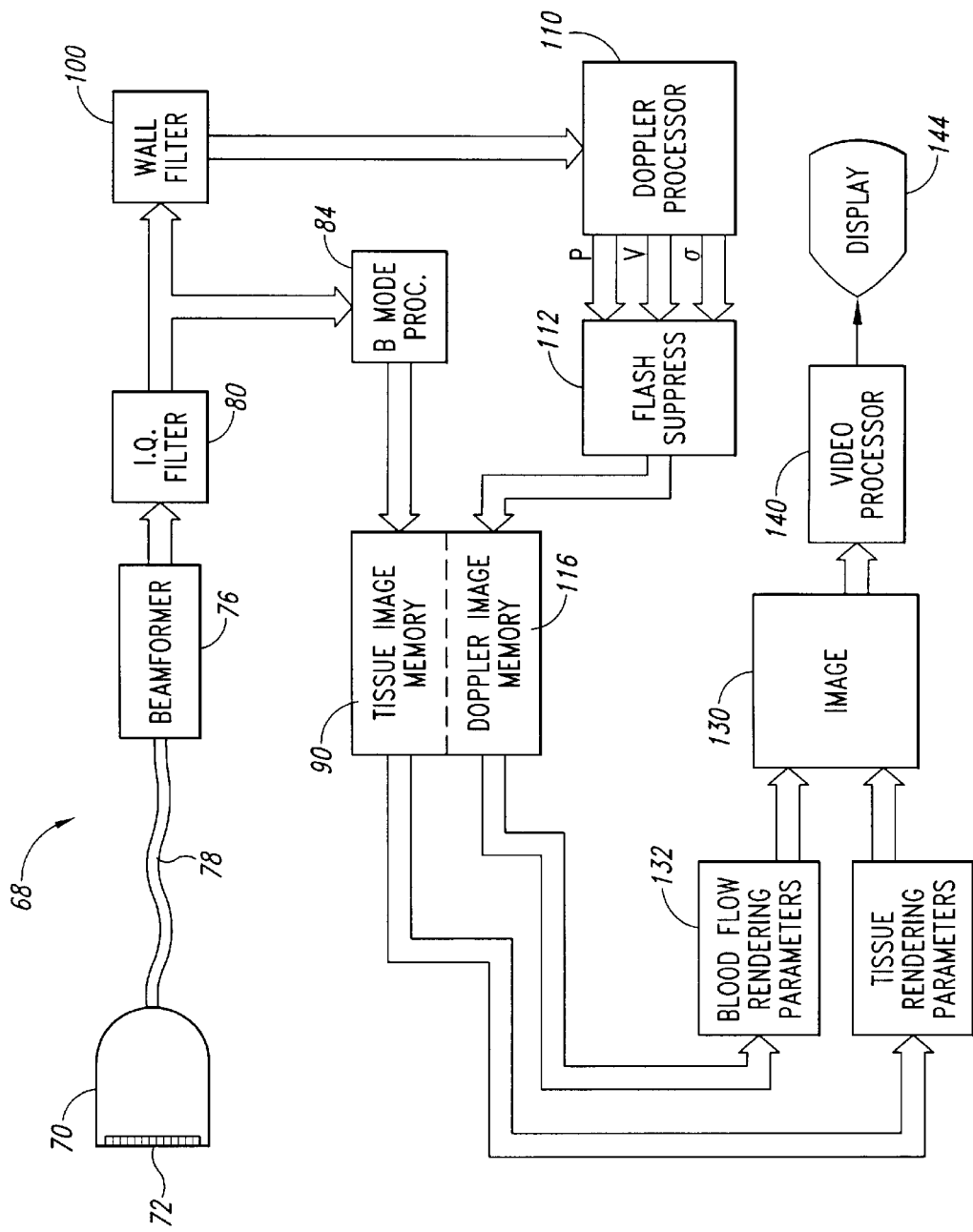
FIG. 6 is a block diagram of an ultrasound imaging system according to one embodiment of the invention.

One embodiment of an ultrasonic diagnostic imaging system 68 for obtaining and segmenting a flow image and determining volume flow rate according to the invention is shown in FIG. 6. Referring to FIG. 6, the system 68 includes a scanhead 70 that includes a transducer array 72. As is well-known in the art, the transducer array 72 transmits ultrasonic pulses into the body of a patient and receives back ultrasound echoes. The transducer array 72 is pulsed under the control of and echoes are received by a beamformer 76, which is coupled to the scanhead 70 by a cable 78. Ultrasound beams transmitted and received by the transducer array 72 are steered and focused under control of the beamformer 76, which processes echo signals from a plurality of elements to form scanlines of coherent echo signals. The received echo signals are quadrature detected and filtered by an in-phase, quadrature ("I,Q") filter 80, then processed for B mode display and Doppler display.

For B-mode processing, the I and Q samples are coupled to a B-mode processor 84, which produces grayscale signals with brightness corresponding to the intensity of received echo signals. The grayscale signals are stored in a tissue image memory 90 together with information bearing their spatial relationship to the image field. When a one-dimensional transducer array is used to acquire the echo signals, scanlines of grayscale signals are acquired to form a full planar image, and a sequence of B-mode planar tissue images is stored in the tissue image memory 90. The image planes retain their spatial orientation to each other by being stored in the time or spatial sequence in which they were acquired. When an electronically steered two-dimensional transducer array is used to acquire the echo signals, they may be stored directly in a three-dimensional data matrix. It is also possible for the grayscale signals to form an image of the spherical image surface 28.

For Doppler processing the I and Q samples undergo highpass filtering in a wall filter 100, then are assembled in ensembles of Doppler data in a Doppler processor 110. The data ensembles are processed by a conventional Doppler technique, such as autocorrelation or Fourier transform processing, to produce Doppler signals of parameters such as Doppler power (P), velocity (v), or variance ($\sigma$). The Doppler signals are processed to remove motion artifacts in a flash suppresser 112, then stored in a Doppler image memory 116 together with information bearing the spatial relationship of the Doppler signals to the image field. In a preferred embodiment, scanlines of Doppler signals are acquired to form the 3-D flow image 26 in a spherical image surface, and a sequence of data corresponding to the vessel flow image 26 are stored in the Doppler image memory 116. The flow images retain their spatial orientation to each other by being stored in the Doppler image memory 116 in the time or spatial sequence in which they were acquired.

The data corresponding to the B-mode images stored in the tissue image memory 90 and the data corresponding to the 3-D flow images stored in the Doppler image memory 116 are then coupled to an image processor 130. The image processor 130 converts the data corresponding to the 3-D flow images to data corresponding to a projection of the 3-D flow images onto a plane, thereby producing data corresponding to a 2D flow image. The image processor 130 then combines the 2-D flow image data with the B-mode image data from the tissue image memory 90. The image processor 130 then generates data corresponding to a rendering of a composite image composed of a 2-D flow image superimposed on B-mode image. The rendering process may be performed in accordance with rendering parameters stored in rendering parameter storage areas 132 and 134. As described in U.S. Pat. No. 5,720,291, these parameters control the manner in which each type of image information will be processed in the rendering. For instance, the user may enter values for the intensity or velocity thresholds to be imparted to each type of image information.

Data corresponding to the composite B-mode image and 2-D flow image are coupled to a video processor 140 that converts the data to appropriate signals, such as NTSC or SVGA signals, for use by a display 144, such as a cathode ray tube display. The composite B-mode image and 2-D flow image are then shown on the display 144.

As previously explained, once the composite image is visible on the display 144, the image processor 130 can automatically segment the image by creating a template that approximately overlies the inner periphery of the blood vessel. The size of the template can then be adjusted by scaling it, and/or the shape of the template can be adjusted by the user, as explained above.

The image processor 130 can also calculate the volume flow rate of blood flowing thorough the blood vessel 10 within the area bounded by the template. The image processor 130 makes this calculation by integrating the blood flow velocity over the area bounded by the template. The image processor 130 then causes the volume flow rate value to be displayed on the display 144 in appropriate units, such as ml/sec.

In the embodiment of the present invention described first above, acquisition is by an electronically steered 2D array transducer, enabling the projected flow image 44 to be rendered and shown in real time. The template 64 can be applied to the real time image to obtain instantaneous measurements of the vessel flow in units such as ml/sec. A number of these instantaneous measurements can be integrated over a period of time to provide a measure such as stroke volume. For instance, integrating the instantaneous measurement made over a cardiac cycle will produce a measure of stroke volume in ml/heartbeat. In another embodiment of the present invention acquisition is performed by a 1D array transducer which acquires planar images, and the image plane is swept through the vessel 10 to acquired three dimensional data. As the image plane is swept through the vessel, flow estimates can be performed and continually updated as additional planes are interrogated. For example, the scanhead is moved so that the image plane cuts through the vessel 10, and Doppler measurement are made along a nonlinear line or curve through the measurement volume 22. Effectively, velocity information is acquired from a single cut plane through the measurement volume. From the intersections of the nonlinear line with the vessel walls, the center of the vessel along the nonlinear line is geometrically calculated. The velocity values on the nonlinear line are then projected onto a straight line which is normal to the vessel walls to produce a velocity profile along the straight line. By assuming that the vessel is axi-symmetric, the velocity values along the straight line are used to estimate the flow through the vessel by applying the velocity values to an assumed circular vessel area and integrating the velocity over this area. This will produce a first estimate of flow.

The scanhead is moved to rock, rotate, or sweep the image plane through the vessel at different angular orientations to the vessel 10, and the process repeated. Each new planar position will reveal further detail of the nonsymmetry of the vessel, that is, the variance of the vessel diameter from a true circle. The additional velocity estimates are then used to update the flow estimate, which can be done as frequently as with the acquisition of every new planar acquisition. The flow estimate updates will occur in substantially real time as new data from additional scanhead positions is acquired. A weighted average is taken of the plurality of velocity measurements, with the weighting being a function of the rotational or angular step between the different acquisition planes.

Since the manual or mechanical sweeping of image planes through the vessel will occur over several or many heart cycles, these flow measurements will not be instantaneous values. Rather, they will be estimates of the flow over a period of time. In accordance with another aspect of the present invention, the scanhead is maintained in each planar orientation for up to a full heart cycle with ECG gating, or longer without gating to measure the velocity over at least a heart cycle. Temporal averaging of the velocity information will provide a longer term measurement, such as the flow through the vessel in ml/min. After the image data has been acquired a three dimensional reconstruction is performed by the image processor 103. A sample surface intersecting the vessel of interest and which is orthogonal to the scanning beams is selected in accordance with the geometry of the scanning beam pattern and the scanning motion. For example, if a linear array transducer is translated to acquire the image data the sample surface will be planar. If a linear array transducer is rocked to acquire the image data the sample surface will be flat in one dimension and curved in the orthogonal direction. Optimally, every point on the sample surface where velocity is measured is normal to the acquiring scanning beam. The sample surface is projected onto a planar surface for display, masked if desired to delineate the flow area, and the velocity information is accumulated, averaged, or integrated to produce a measure of flow volume.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of obtaining an image of volume flow in a blood vessel, the method comprising:

using a two-dimensional ultrasound scanhead to obtain a three-dimensional Doppler image of blood flow velocity in a relatively narrow sample volume intersecting the lumen of the blood vessel, the sample volume being a predetermined distance from the scanhead;

electronically projecting the Doppler image onto a planar surface; and creating an image of the electronically projected Doppler image.

2. The method of claim 1, wherein using further comprising:

obtaining a sample volume containing a sample surface of points which are substantially normal to the direction of transmitted ultrasound beams.

3. The method of claim 2 wherein the act of creating an image of the tissue comprises:

acquiring ultrasound signals from tissue which is adjacent to the lumen; and creating an image of tissue in superposition with the image of the electronically projected the Doppler image.

4. The method of claim 1, further comprising automatically segmenting the image of the electronically projected the tissue image in superposition with the image of the electronically projected the Doppler image by creating a template approximately overlying a wall of the blood vessel.

5. The method of claim 4 further comprising adjusting the template.

6. The method of claim 5 wherein the act of adjusting the template comprises scaling the size of the template.

7. The method of claim 5 wherein the act of adjusting the template comprises adjusting the position of a selected portion of the template.

8. The method of claim 4, further comprising integrating the blood flow velocity within the template to determine the blood volume flow rate within the blood vessel, and displaying a value corresponding to the blood volume flow rate.

9. The method of claim 1, wherein the scanhead comprises a two-dimensional array scanhead.

10. The method of claim 1, further comprising integrating the blood flow velocity within the lumen to determine the blood volume flow rate within the blood vessel, and displaying a value corresponding to the blood volume flow rate.

11. A method for estimating blood flow in a blood vessel, comprising:

acquiring velocity information from a blood vessel by moving a one dimensional array transducer to different orientations relative to a blood vessel;

projecting the velocity information acquired at each orientation onto a straight line to produce a velocity profile;

estimating the flow rate from the projected velocity information in combination with velocity information acquired from a different orientation to produce an updated estimate of flow rate; and displaying the flow rate estimate.

12. The method of claim 11 wherein estimating comprises producing a weighted average of velocity information acquired from a plurality of orientations, the weighting being a function of the rotational or angular step between different transducer orientations.

13. The method of claim 11, wherein acquiring further comprises acquiring velocity information at each orientation for a period of time.

14. The method of claim 13, further comprising integrating the converted Doppler data corresponding to blood flow velocity within the template to determine the blood volume flow rate within the template, and displaying a value corresponding to the blood volume flow rate.

15. The method of claim 13 further comprising adjusting the template.

16. The method of claim 15 wherein the act of adjusting the template comprises scaling the size of the template.

17. The method of claim 15 wherein the act of adjusting the template comprises adjusting the position of a selected portion of the template.

18. The method of claim 11, further comprising integrating the converted Doppler data corresponding to blood flow velocity within the image to determine the blood volume flow rate within the vessel, and displaying a value corresponding to the blood volume flow rate.

19. A method of determining the volume flow rate of blood flowing through a blood vessel, comprising:

using a two-dimensional array transducer to obtain data corresponding to a three-dimensional Doppler image of blood flow velocity in a relatively narrow sample volume intersecting the entire lumen of the blood vessel, the sample volume being a fixed distance from the transducer;

processing the data corresponding to the three-dimensional Doppler image to provide data corresponding to a projection of the three-dimensional Doppler image onto a plane thereby providing two-dimensional Doppler image data corresponding to a three-dimensional Doppler image of blood flow velocity in a surface; and processing the two-dimensional Doppler image data to integrate the velocity of blood flow shown in the two-dimensional Doppler image across an area of blood flow to determine the blood volume flow rate.

20. The method of claim 19, further comprising displaying the two-dimensional Doppler image.

21. The method of claim 19, further comprising processing the two-dimensional Doppler image data to segment the blood flow from the blood vessel, and wherein the act of processing the two-dimensional Doppler image data to integrate the velocity of blood flow in the segmented blood flow.

22. A system for displaying a volume flow image of blood flowing through a blood vessel, the system comprising:

a scanhead having a plurality of transducer elements;

a beamformer coupled to receive the echo signals from the scanhead and to generate output signals corresponding thereto;

a Doppler processor coupled to the beamformer, the Doppler processor being operable to generate data corresponding to an image of the velocity of blood flowing through the blood vessel in a nonplanar surface intersected by the blood vessel;

an image processor coupled to the Doppler processor, the image processor being operable to generate 2-D Doppler image data corresponding to the projection of the blood flow velocity in the nonplanar surface onto a plane; and a display displaying an image corresponding to the 2-D Doppler image data.

23. The system of claim 22 wherein the image processor is further operable to integrate the 2-D Doppler image data over the area of the blood vessel to determine the blood volume flow rate through the blood vessel.

24. The system of claim 22 wherein the image processor is further operable to automatically segment the composite image by means of a template delineating the blood flow of the blood vessel.

25. The system of claim 24 wherein the image processor is further operable to adjust the template by scaling the size of the template.

26. The system of claim 24 wherein the image processor is further operable to adjust the position of a selected portion of the template.

27. The system of claim 24 wherein the image processor is further operable to integrate the 2-D Doppler image data over the area of the template to determine the blood volume flow rate through a portion of the blood vessel encompassed by the template.

28. The system of claim 22 wherein the scanhead comprises a two-dimensional array scanhead.

29. The system of claim 22 further comprising a 3-D image processor responsive to the velocity data produced by the Doppler processor which operates to produce a 3-D image which includes the nonplanar surface.

30. The system of claim 22 wherein the scanhead is operable to transmit a plurality of beams directed to the blood vessel; and wherein the nonplanar surface comprises a plurality of points which are substantially normal to beams transmitted by the scanhead.

31. A composite ultrasound image comprising a cross-sectional ultrasound image of a blood vessel superimposed on a 2-D Doppler image resulting from a projection onto a plane of a three-dimensional Doppler image showing the velocity of blood flowing through the blood vessel.

32. The composite ultrasound image of claim 31 wherein the three-dimensional Doppler image comprises an image taken through a relatively narrow spherical sample volume extending across the blood vessel.

33. The composite ultrasound image of claim 31, further comprising a segmenting template superimposed on the image to delineate a boundary between the blood vessel and the blood flowing through the blood vessel.

* * * * *